US00PP13063P2

(12) United States Plant Patent
Radler

(10) Patent No.: US PP13,063 P2
(45) Date of Patent: Oct. 8, 2002

(54) SHRUB ROSE PLANT NAMED 'RADSUN'

(76) Inventor: William J. Radler, 10020 W. Meadow Dr., Greenfield, WI (US) 53228

( * ) Notice: Subject to any disclaimer, the term of this patent is extended or adjusted under 35 U.S.C. 154(b) by 0 days.

(21) Appl. No.: 09/760,801

(22) Filed: Jan. 17, 2001

(51) Int. Cl.[7] ..... A01H 5/00
(52) U.S. Cl. ..... Plt./104
(58) Field of Search ..... Plt./104

(56) References Cited

U.S. PATENT DOCUMENTS

PP6,793 P * 5/1989 Moore ..... Plt./104
PP9,637 P * 9/1996 Olesen et al. ..... Plt./104

* cited by examiner

*Primary Examiner*—Bruce R. Campell
*Assistant Examiner*—Wendy C. Baker

(57) ABSTRACT

A new and distinct variety of landscape shrub rose plant is provided which forms in abundance on a substantially continuous basis attractive clusters of semi-double informal blossoms that are clear yellow in coloration. The vegetation is strong and vigorous. A compact mounding shrub growth habit is displayed. Attractive dense medium green foliage having a satin finish is formed. Excellent resistance to Black Spot is exhibited. Attractive ornamentation in the landscape is provided.

12 Drawing Sheets

BOTANICAL/COMMERCIAL CLASSIFICATION

Figure 1:
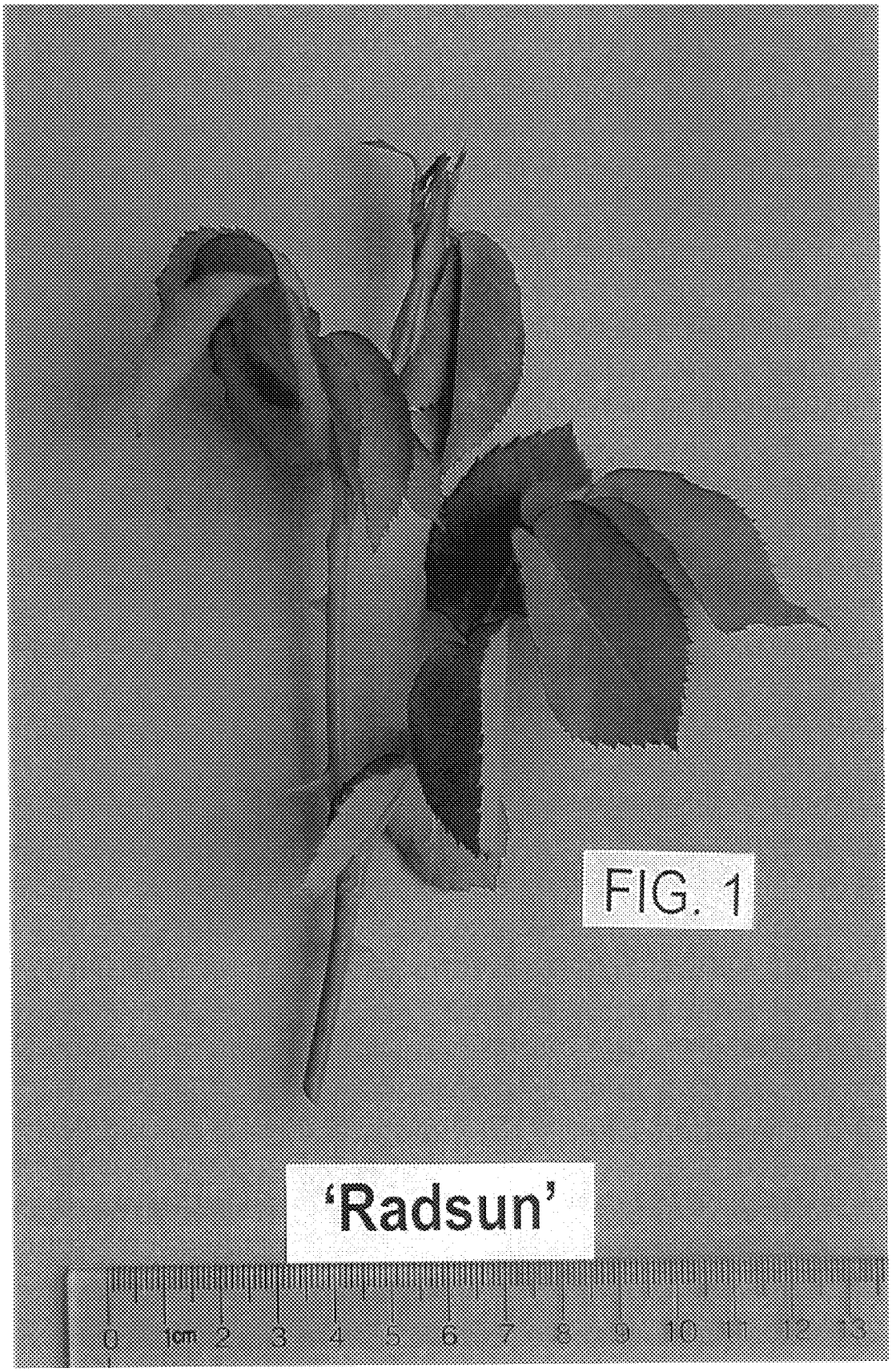

*Rosa hybrida*/Landscape Spray Rose.

VARIETAL DENOMINATION cv. 'Radsun'.

SUMMARY OF THE INVENTION

The new variety of *Rosa hybrida* landscape shrub rose plant of the present invention was created by artificial pollination wherein two parents were crossed which previously had been studied in the hope that they would contribute the desired characteristics. The female parent (i.e., the seed parent) of the new variety was an unnamed seedling (non-patented in the United States). The male parent (i.e., the pollen parent) of the new variety was another unnamed seedling (non-patented in the United States). The parentage of the new variety can be summarized as follows:

Unnamed Seedling×Unnamed Seedling.

The seeds resulting from the above pollination were sown and small plants were obtained which were physically and biologically different from each other. Selective study resulted in the identification of a single plant of the new variety.

It was found that the new variety of landscape shrub rose plant of the present invention possesses the following combination of characteristics:

(a) Abundantly forms on a substantially continuous basis attractive clusters of semi-double informal blossoms that are clear yellow in coloration,
(b) Exhibits a compact mounding shrub growth habit,
(c) Forms vigorous vegetation,
(d) Forms dense medium green foliage having a satin finish, and
(e) Exhibits excellent resistance to Black Spot.

The new variety well meets the needs of the horicultural industry. It can be grown to advantage as attractive ornamentation in parks, gardens, public areas, and residential landscapes. It is particularly well suited for growing in the landscape when informal ornamentation is desired. The clear yellow blossoms contrast nicely with the medium green foliage having a satin finish.

The characteristics of the new variety have been found to be homogeneous and stable and are strictly transmissible at West Grove, Pa. by asexual propagation such as budding, grafting, and cuttage from one generation to another. The plant propagates well and grows very well on its own roots when propagated from cuttings.

The new variety has been named the 'Radsun' variety. The new variety is being marketed under the CAREFREE SUNSHINE trademark.

'Radsun' has not been observed under all possible environmental conditions to date. Accordingly, it is possible that the phenotype may vary somewhat with variations in the environment, such as temperature, light, etc.

BRIEF DESCRIPTION OF THE PHOTOGRAPHS

The accompanying photographs show, as nearly true as it is reasonably possible to make the same in color illustrations of this character, typical specimens of the plant parts of the new variety. The rose plants of the new variety illustrated herein were four years of age and were grown in a greenhouse at West Grove, Pa. while grafted on Rosa 'Dr. Huey' rootstock. The photographs were prepared on Apr. 9, 2002, and dimensions in centimeters are indicated at the bottom of each photograph.

Figures 2, 3, 4, 5:
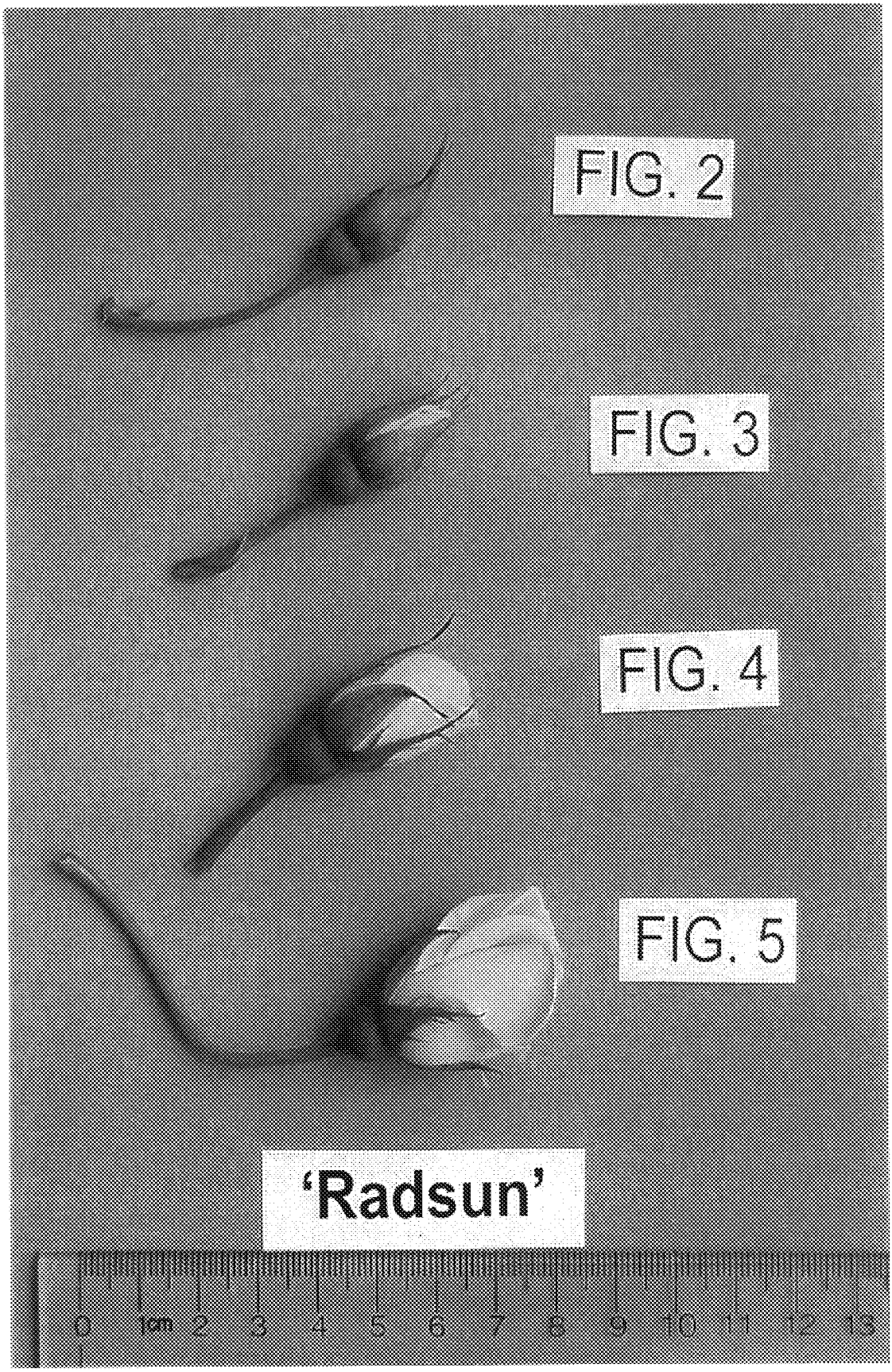
Figure 6:
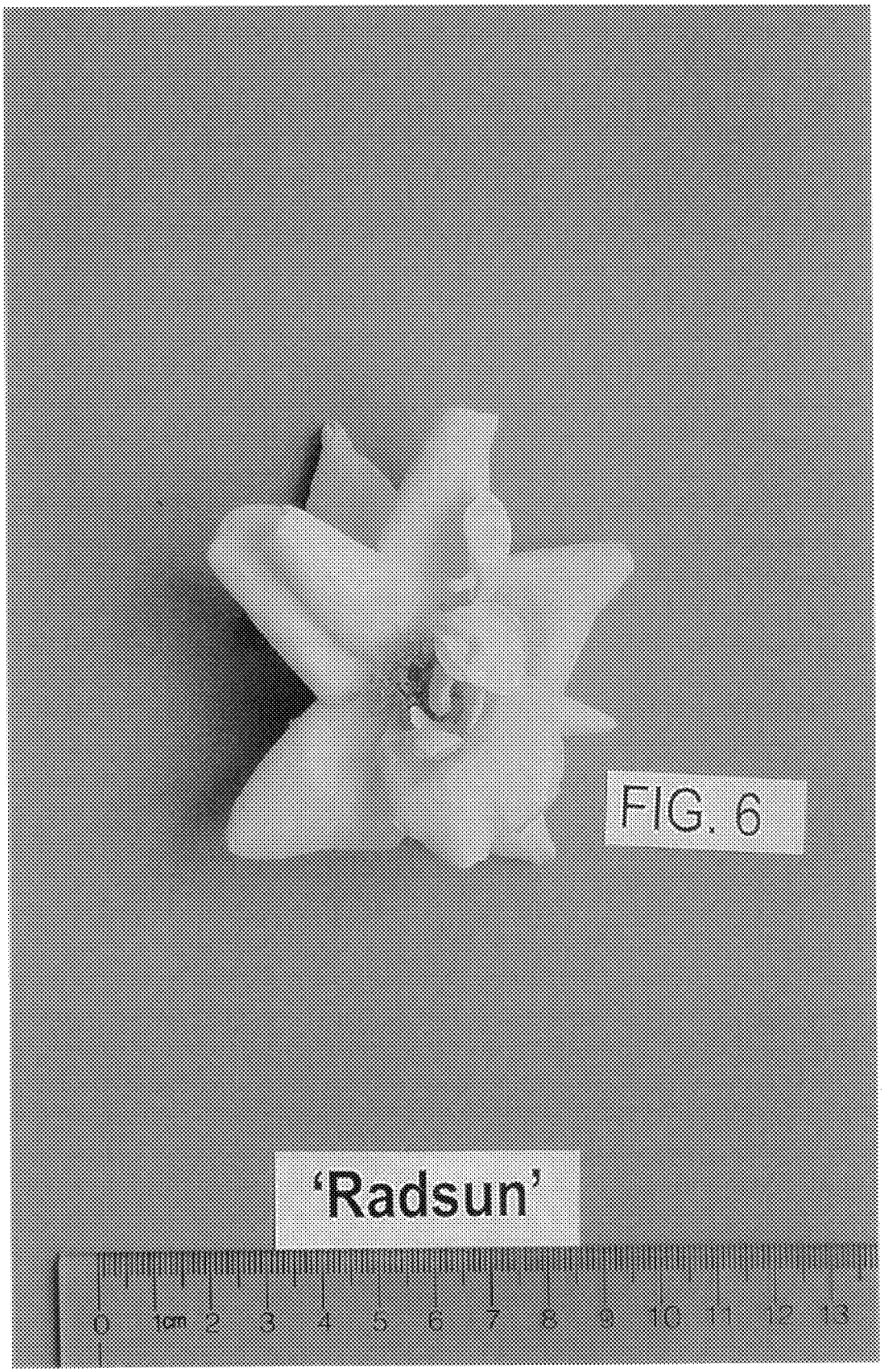
Figure 7:
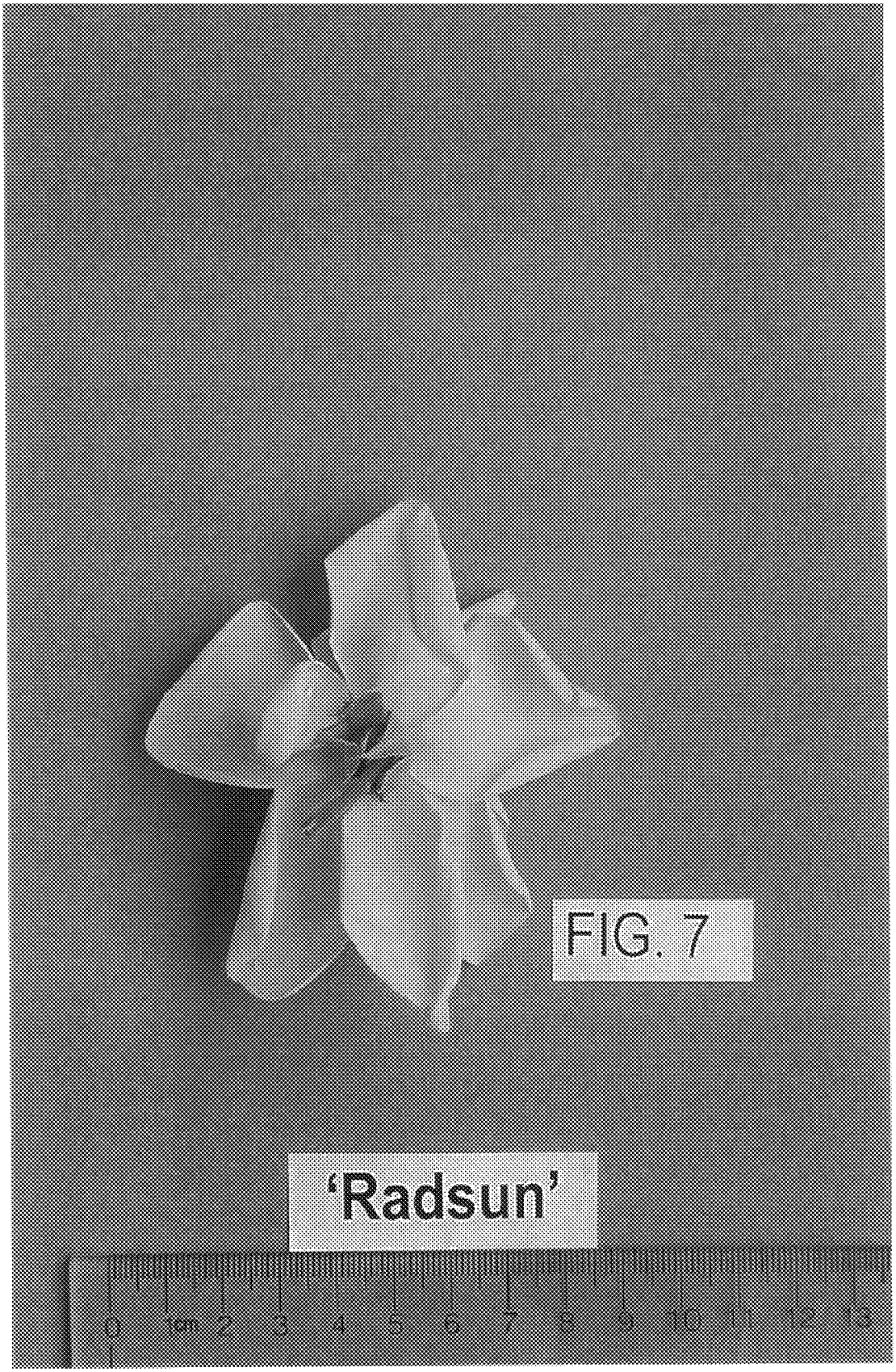
Figures 8, 9:
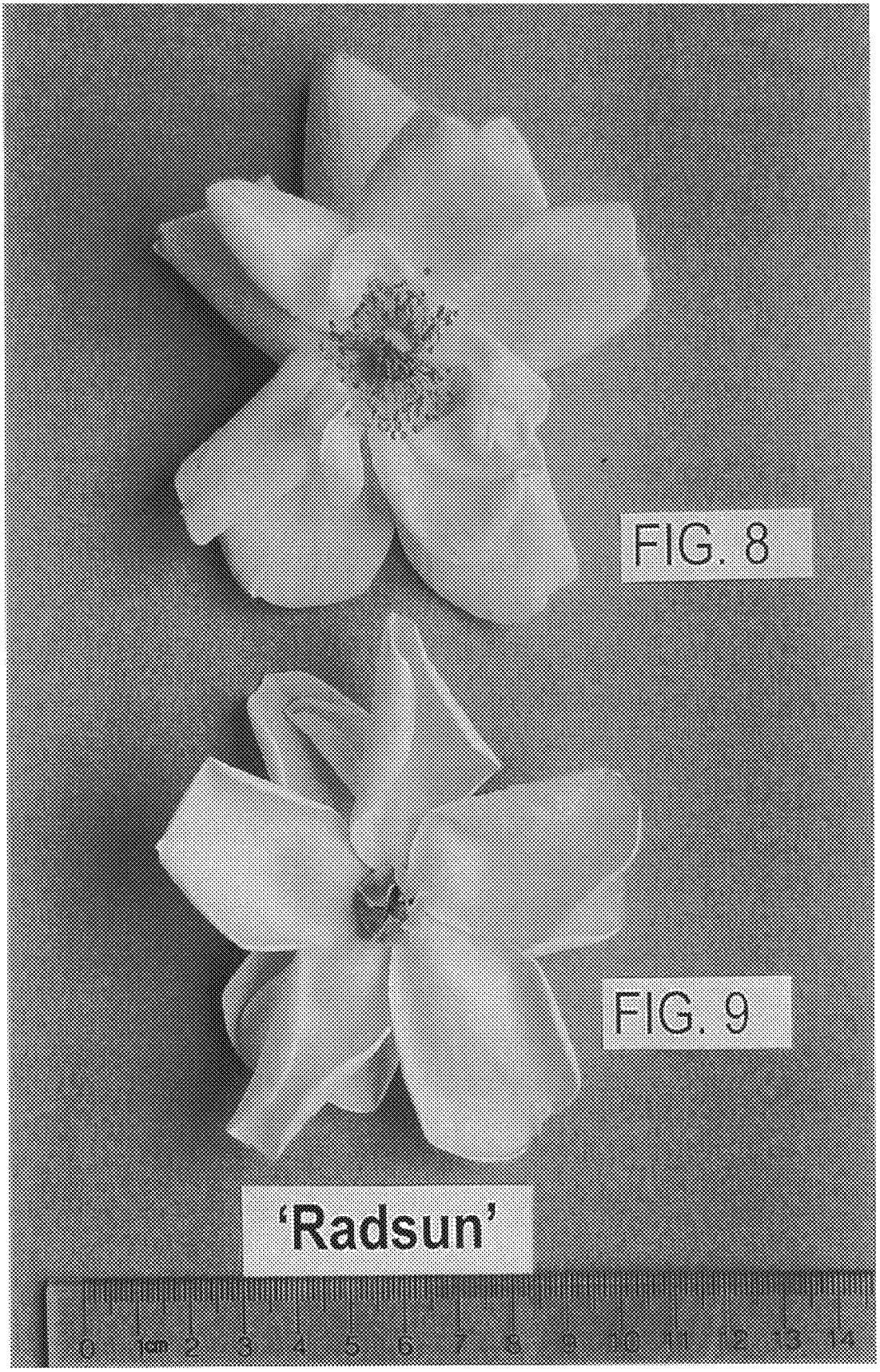
Figures 10, 11:
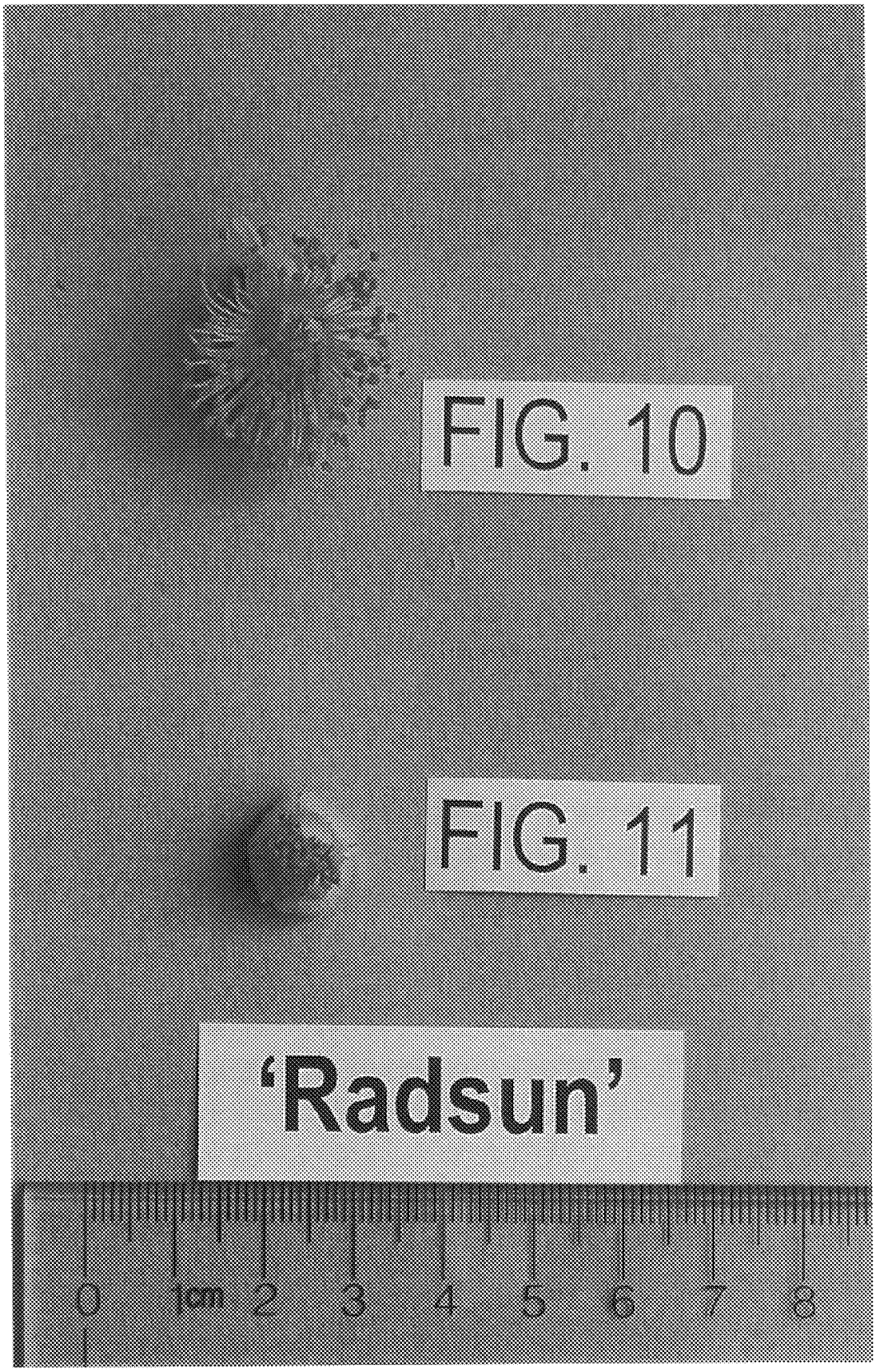
Figure 12:
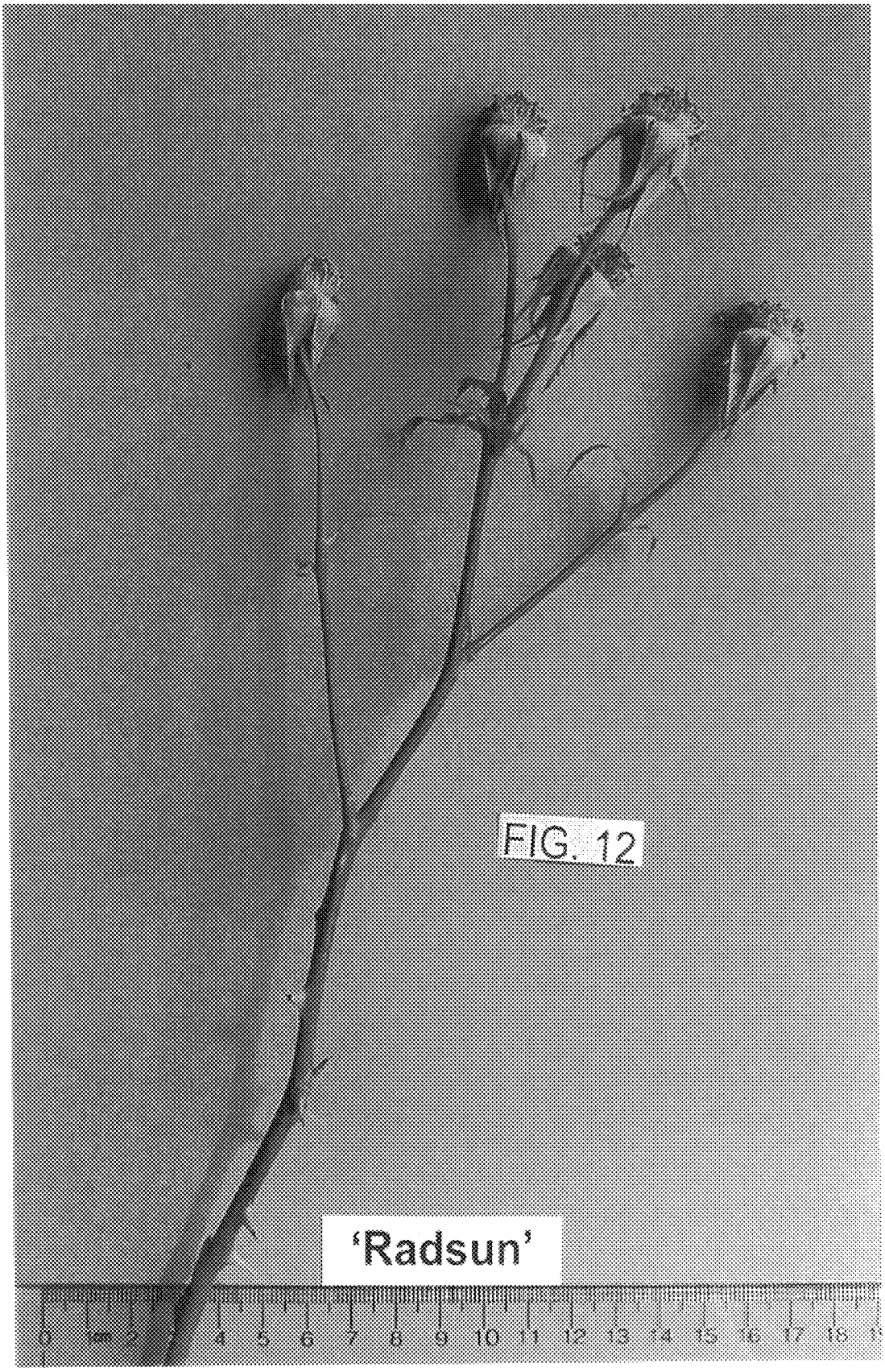
Figure 13:
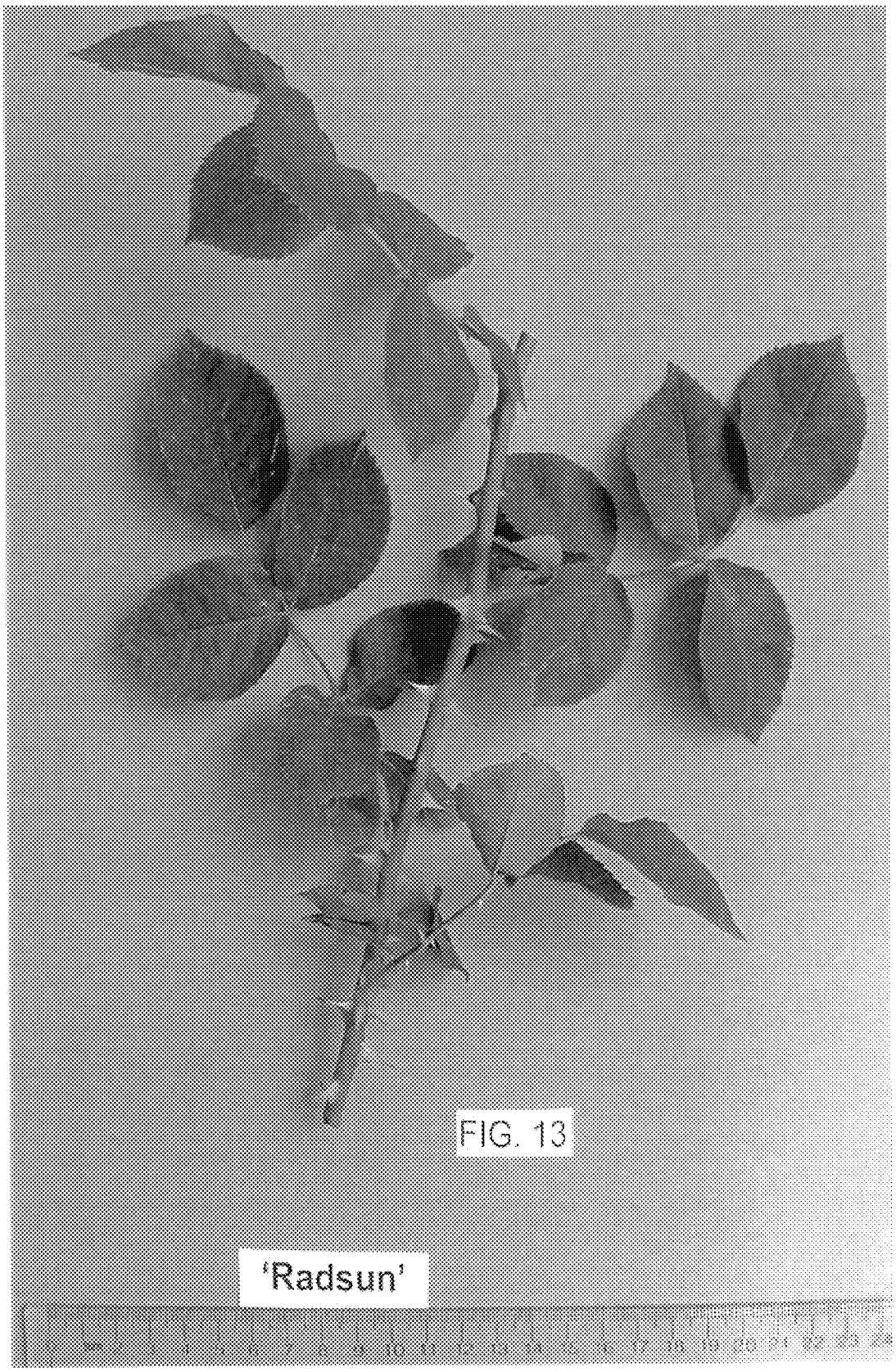
Figure 14:
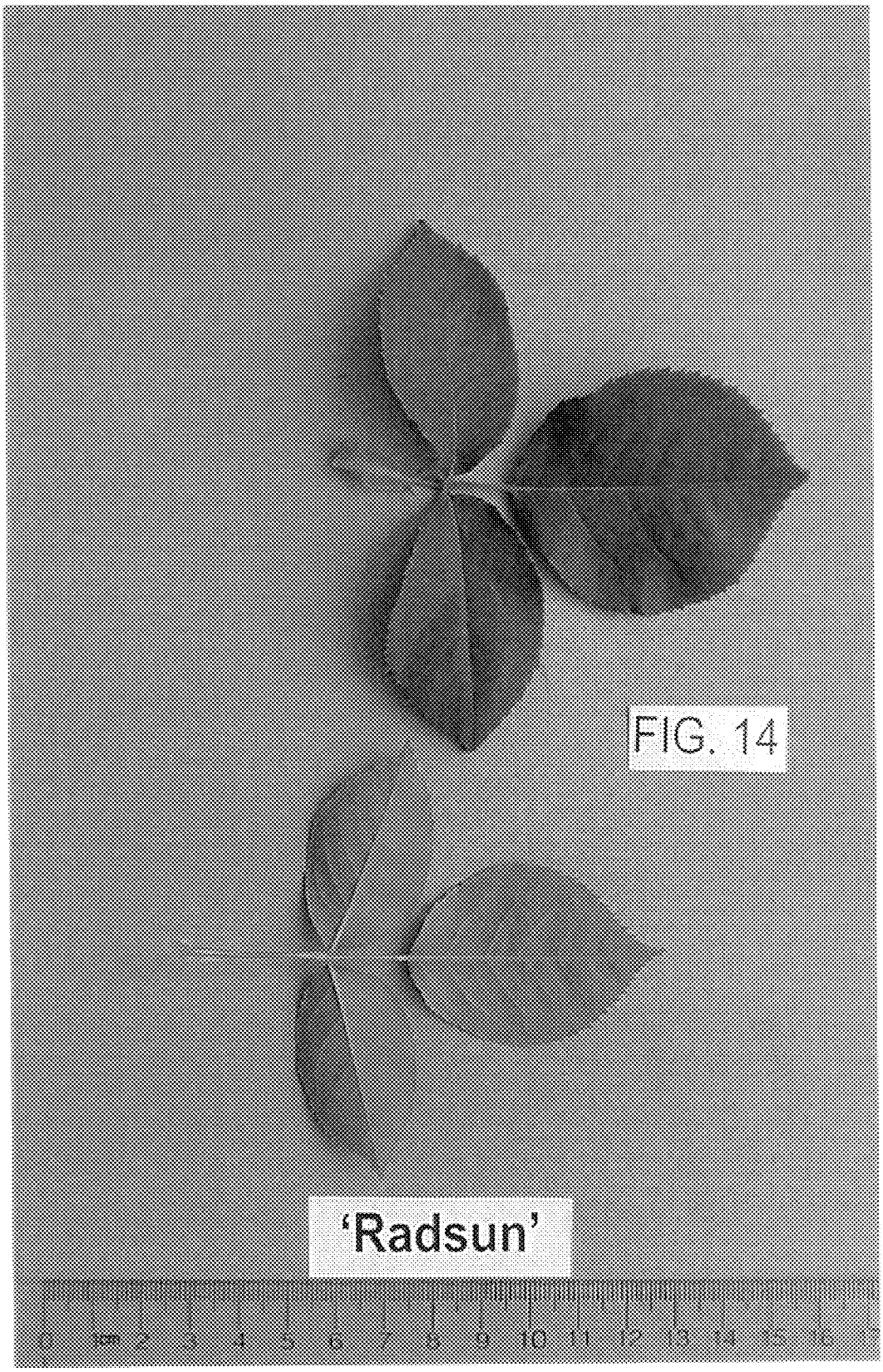
Figure 15:
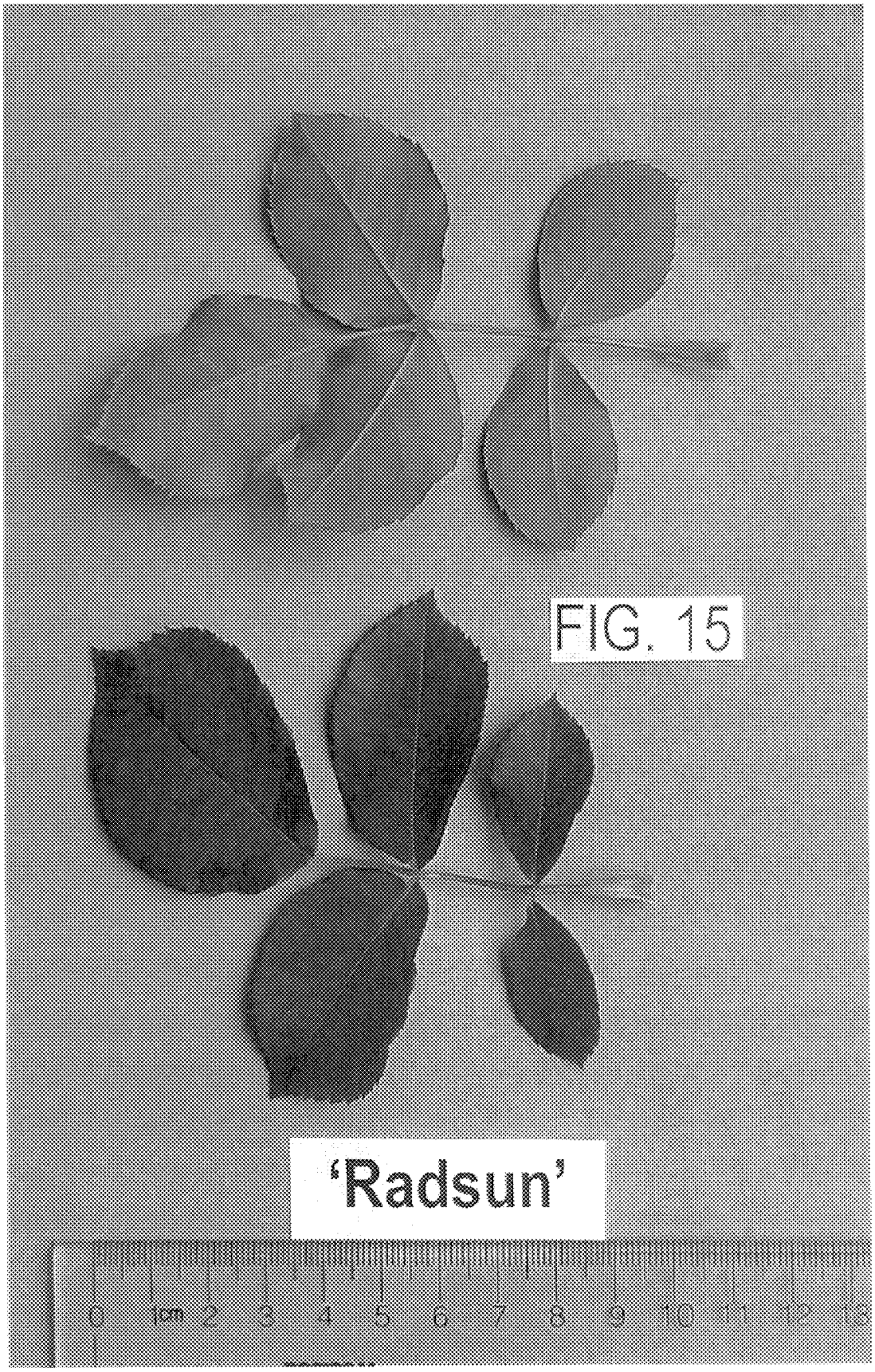
Figure 16:
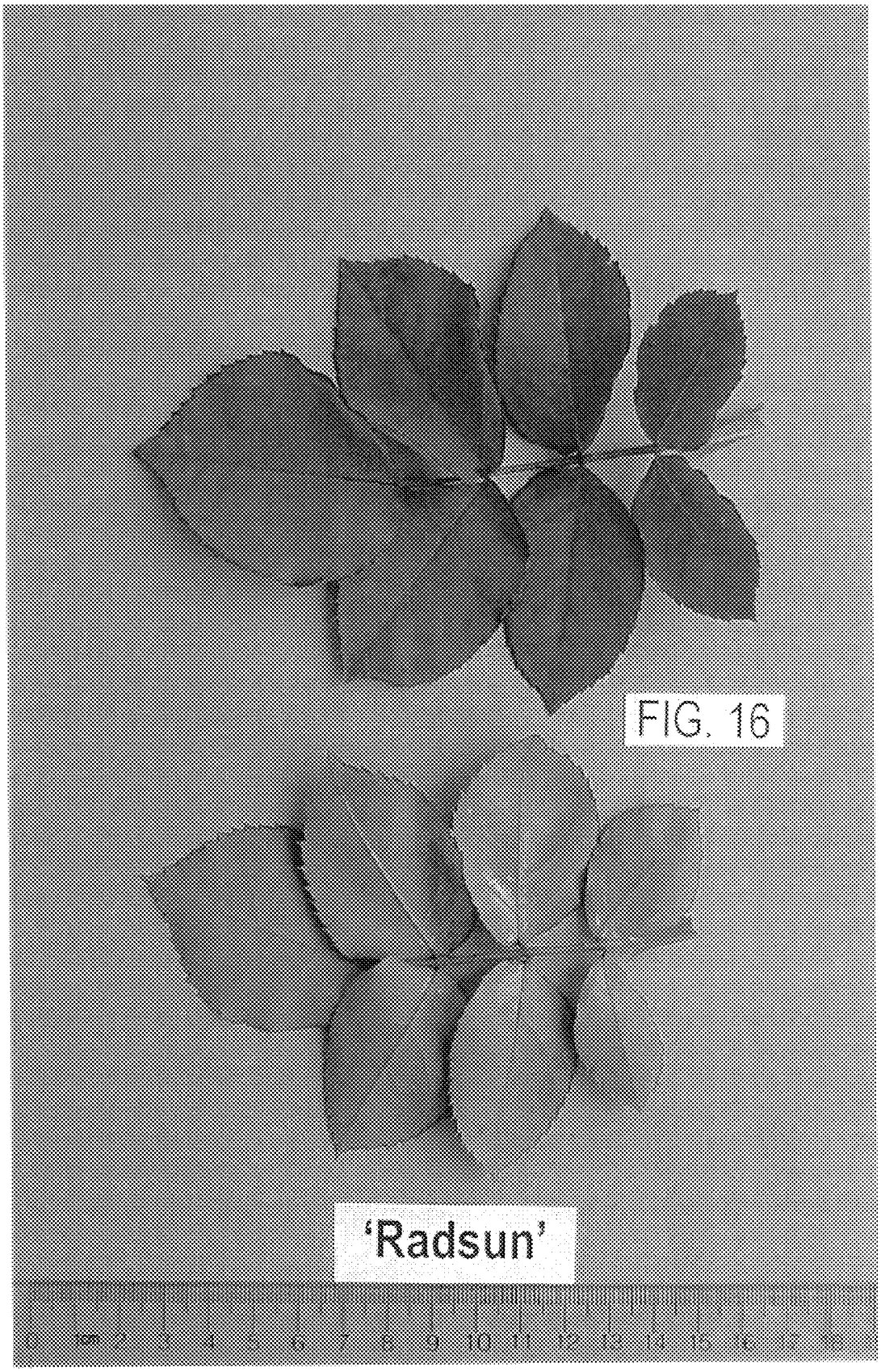
Figure 17:
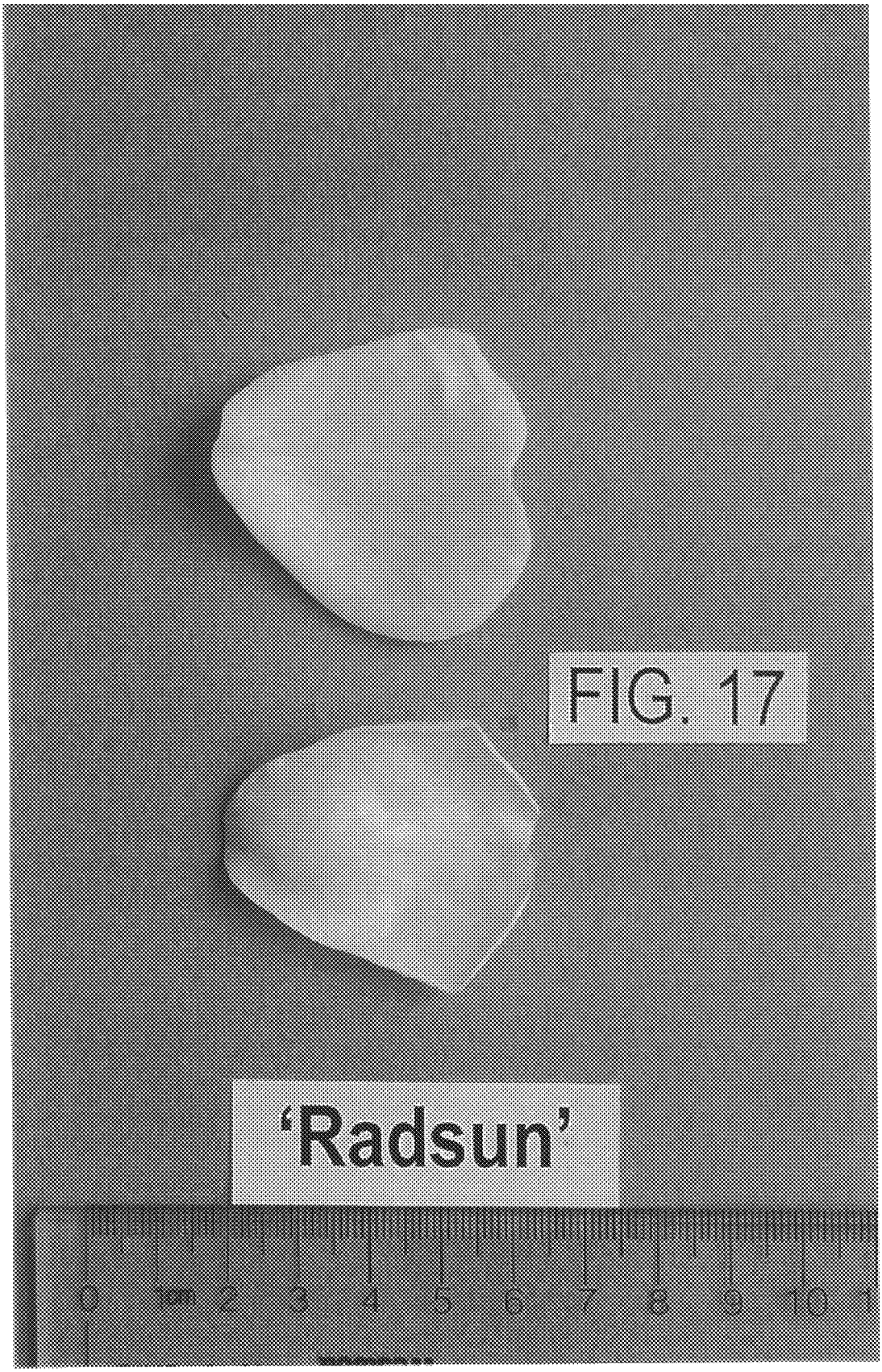

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem following petal drop;

FIG. 13—illustrates a specimen of a main branch with foliage;

FIG. 14—illustrates specimens of leaves with three leaflets—plan view—upper surface top and under surface bottom;

FIG. 15—illustrates a specimen of a leaf with five leaflets—plan view—under surface (top) and—plan view—upper surface (bottom);

FIG. 16—illustrates a specimen of a leaf with seven leaflets—plan view—upper surface (top) and—plan view—under surface (bottom); and FIG. 17—illustrates specimens of maturing petals.

DETAILED DESCRIPTION

The chart used in the identification of colors is that of The Royal Horticultural Society (R.H.S. Colour Chart). The description is based on the observation of two-year old specimens the new variety during October while grown outdoors on their own roots at West Grove, Pa.

Plant:

*Height.*—Approximately one meter on average at the end of the growing season.

*Width.*—Approximately one meter on average at the end of the growing season.

*Habit.*—Compact and mounding shrub.

Branches:

*Color.*—Young stems: Yellow-Green Group 144B with flecks of Greyed-Purple Group 184B. Adult wood: Yellow-Green Group 144B.

*Thorns.*—Shape: needle-shaped. Size: approximately 5 to 8 mm on average. Quantity: commonly approximately 25 true thorns on average per 30 cm of stem. Color: Greyed-Red Group 161C with highlights of Red Group 51A.

Leaves:

*Stipules.*—Parallel with auricle facing outwards.

*Petioles.*—Upper surface: Yellow-Green Group 144B. Under surface: Yellow-Green Group 144B with flecks of Greyed-Purple Group 184C.

*Rachis.*—Glandular and commonly with small prickles on the upper surface. The prickle size commonly varies from approximately 1 to 3 mm with up to 4 prickles on the rachis of three-leaflet leaves and up to 7 prickles on the rachis of seven-leaflet leaves. The prickles commonly are slightly recurved and tend to point towards the stem. The glands commonly are globose and reddish in coloration and are present on both surfaces while borne on short stalks of approximately 0.3 mm.

*Leaflets.*—Number: 3, 5, and 7. Shape: ovate with rounded base and acuminate apices. Serration: regular. Texture: consistent. Overall appearance: very dense, medium green in coloration, and with a satin finish. Color (young foliage): upper surface: Yellow-Green Group 146A with a tint of Greyed-Purple Group 184D at the edges. under surface: near Yellow-Green Group 146B with a tint of Greyed-Purple Group 184D at the edges. Color (adult foliage): upper surface: Green Group 139A. under surface: Yellow-Green Group 146C. Midrib: commonly bears glands on the ventral surface similar to those present on the rachis. Small prickles of approximately 0.4 to 0.8 mm commonly also are present on the ventral surface of the midrib.

Inflorescence:

*Number of flowers.*—Commonly approximately 4 per floral stem in a cluster.

*Peduncle.*—Medium in size, Yellow-Green Group 144B with some prickles, and approximately 5 cm in length on average.

*Sepals.*—Upper surface: commonly between Yellow-Green Group 144A and 144B in coloration. Under surface: commonly between Yellow-Green Group 144B and 144C in coloration with pubescence of White Group 155D.

*Buds.*—Shape: ovoid. Length: approximately 2.5 cm on average. Size: small to medium. Color (when opening): upper surface: Sulphur Yellow, near Yellow Group 6A and 6C shading to near 7B and 9A towards the base. under surface: near Yellow Group 7B and 8A shading to near 6A and 7A towards the base.

*Flower.*—Form: semi-double and informal. Diameter: approximately 8 cm on average. Color (when opening begins): upper surface: Sulphur Yellow, near Yellow Group 6A and 6C shading to near 7B and 9A towards the base. under surface: near Yellow Group 7B and 8A shading to near 6A and 7A towards the base. Color (when blooming): upper surface: Desden Yellow, near Yellow Group 5C shading to near 5B towards the base. Under surface: Sulphur Yellow, near Yellow Group 6D shading to near 7D towards the base. Color (at end of blooming): upper surface: near Green-Yellow Group 1D and Yellow Group 2D shading to Yellow Group 7D towards the base. under surface: near Yellow Group 2D shading to Yellow Group 4C towards the base. Fragrance: slightly spicy. Petal shape: wedge-shaped with a curled apex. Petal number: approximately 10 on average. Petaloids: sometimes are observed at a frequency of 1 to 5 per bloom and more commonly 1 to 3 per bloom. Stamen number: approximately 70 on average. Anthers: Greyed-Orange Group 163C in coloration. Filaments: Yellow Group 12B in coloration. Pistils: approximately 30 on average. Stigmas: Yellow-Orange Group 20A in coloration. Styles: Yellow Group 12B with highlights of Red Group 52A in coloration. Receptacle: separate and free with achenes on the bottom and wall.

Development:

*Vegetation.*—Commonly vigorous and strong. The level of vigor will vary with the environmental conditions that are encountered.

*Blossoming.*—Abundant and everblooming.

*Resistance to diseases.*—Excellent resistance to Black Spot.

*Hip formation.*—Hips are formed.

I claim:

1. A new and distinct variety of landscape shrub rose plant characterized by the following combination of characteristics:

(a) Abundantly forms on a substantially continuous basis attractive clusters of semi-double informal blossoms that are clear yellow in coloration, (b) Exhibits a compact mounding shrub growth habit, (c) Forms vigorous vegetation, (d) Forms dense medium green foliage having a satin finish, and (e) Exhibits excellent resistance to Black Spot;

substantially as herein shown and described.

* * * * *

'Radsun'
0 1cm 2 3 4 5 6 7 8 9 10 11 12 13

'Radsun'
0 1cm 2 3 4 5 6 7 8 9 10 11 12 13 14

'Radsun'
0
1cm
2
3
4
5
6
7
8

UNITED STATES PATENT AND TRADEMARK OFFICE

CERTIFICATE OF CORRECTION

PATENT NO. : PP 13,063 P2
DATED : October 8, 2002
INVENTOR(S) : William J. Radler It is certified that error appears in the above-identified patent and that said Letters Patent is hereby corrected as shown below:

Title page,
Item [73], insert:
-- [73] Assignee: CP (Delaware), Inc., Wilmington, DE (US) --

Signed and Sealed this

Fourth Day of February, 2003

JAMES E. ROGAN
*Director of the United States Patent and Trademark Office*